United States Patent [19]

Henry et al.

[11] 3,966,973

[45] June 29, 1976

[54] PROCESS FOR DETERMINING AND CONTROLLING THE MOISTURE OF FOOD PRODUCTS

[75] Inventors: William F. Henry, Minneapolis; Gareth J. Templeman, Chanhassen; Roger A. Gorman, Hopkins, all of Minn.; Lawrence Pinaire, Clarksville, Ind.

[73] Assignee: The Pillsbury Company, Minneapolis, Minn.

[22] Filed: Aug. 26, 1974

[21] Appl. No.: 500,971

[52] U.S. Cl. ................................. 426/231; 73/73; 73/169; 324/.5 R
[51] Int. Cl.² ........................................ G01N 33/02
[58] Field of Search ............... 426/231; 73/73, 169

[56] References Cited
UNITED STATES PATENTS

| 2,859,403 | 11/1958 | Kirchner | 73/73 X |
| 2,999,381 | 9/1961 | Chope et al. | 73/73 |

OTHER PUBLICATIONS
Miller et al., "Food Technology" May 1963, pp. 142–145.

Primary Examiner—Raymond N. Jones
Attorney, Agent, or Firm—James V. Harmon; Michael D. Ellwein

[57] ABSTRACT

In the present invention the moisture content of foods is determined and controlled by moving the product continuously past one or both of two sensing devices; a nuclear magnetic resonance sensor and a vector impedance sensor which measures the impedance and phase angle resulting from the application of an alternating current of predetermined frequency. The resulting signals are fed to automatic data processing equipment for determining the moisture content as a function of the frequency in Hertz, the phase angle in degrees expressed from $-90°$ through $0°$ to $+90°$, and optionally the impedance and the NMR liquid content. The resulting signal which varies as the moisture content is used to control the addition of water or solids to the material to thereby regulate its moisture content.

5 Claims, 3 Drawing Figures

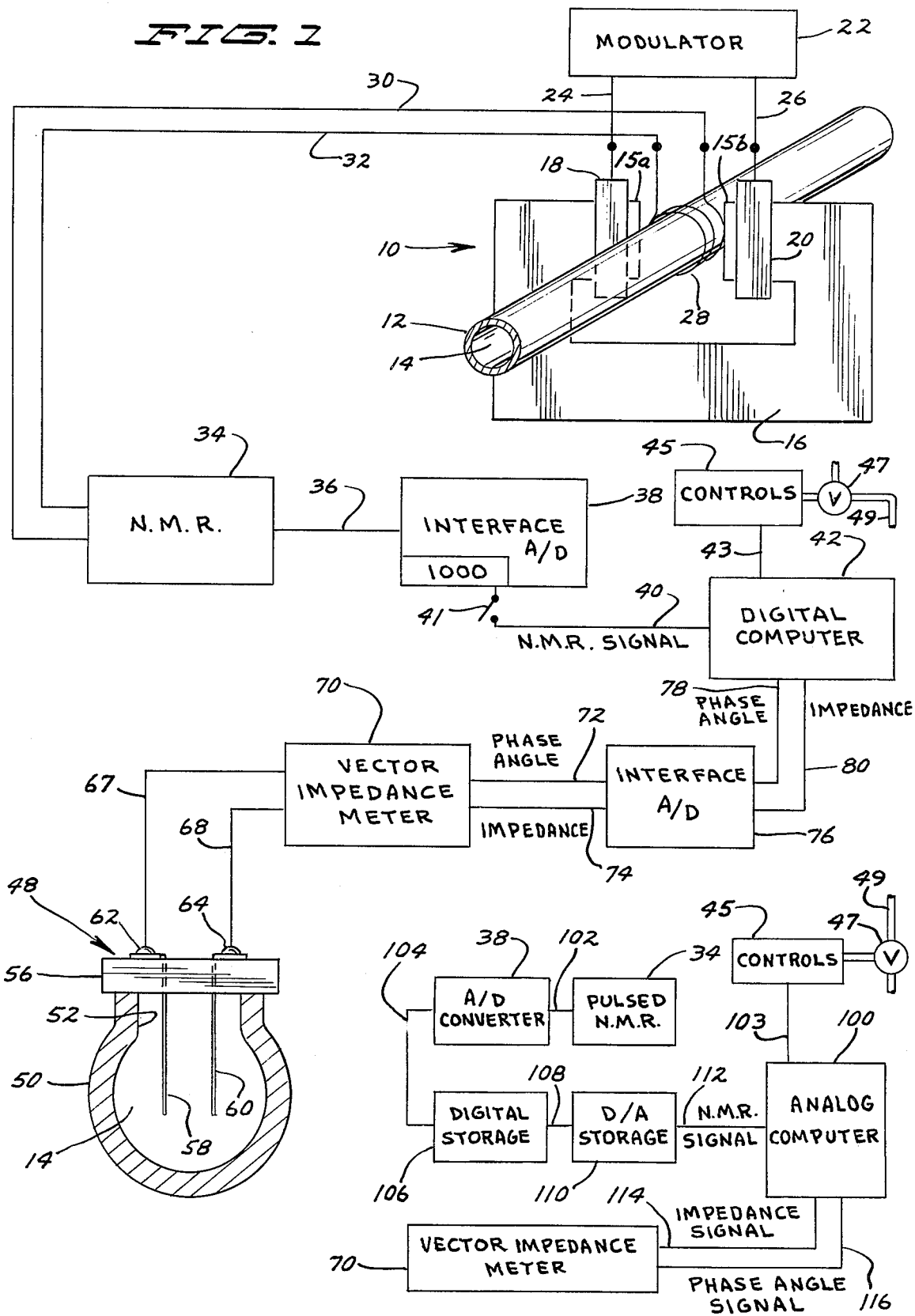

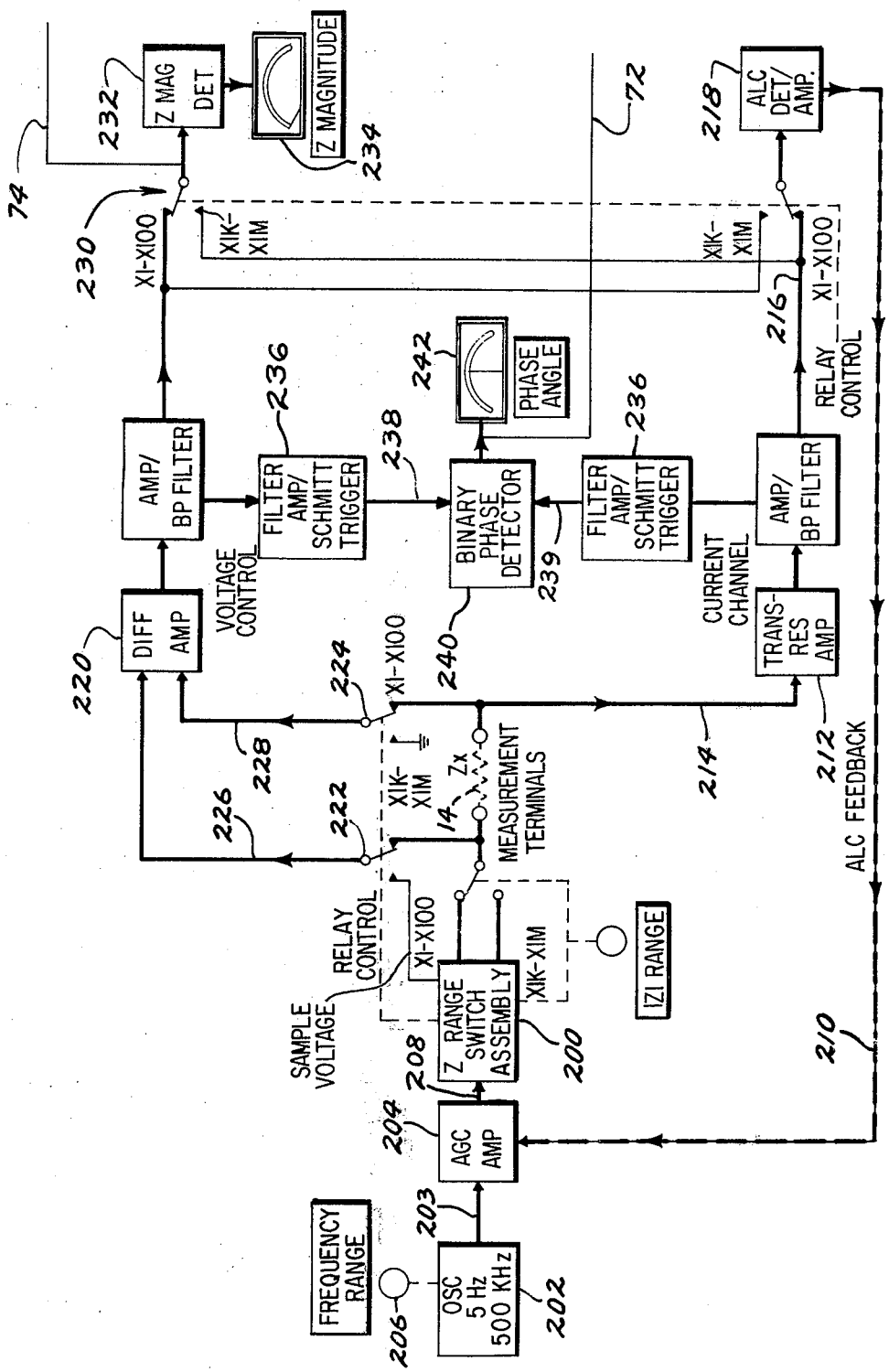

PROCESS FOR DETERMINING AND CONTROLLING THE MOISTURE OF FOOD PRODUCTS

FIELD OF THE INVENTION

The present invention relates to food processing and more particularly to the sensing of moisture in food. The invention is particularly useful in controlling the moisture content of foods during continuous processing.

THE PRIOR ART

In a variety of food products such as biscuit and bread dough, batters including cake, pancake, biscuit batter, and a great many non-flour containing foods such as applesauce, peanutbutter, applebutter, jam, jelly, cooked mashed potato, pudding, frosting, mayonnaise, etc. it is desirable to be able to control the moisture content on a continuous basis during processing, that is to say, during mixing, compounding and cooking prior to packing for shipment. Moisture tests presently available such as those involving drying a small sample of the product in a pan are time consuming, tedious and do not produce instant results nor a record in a form which can be used for adding water or solids as required to reach the desired moisture content. Reflectance tests depend upon the surface character of the material and are thus limited in application. Conductance and dielectric tests often give false readings which result in large part from a non-homogeneous distribution of the water in the product. Moreover, the addition of ions is read as more moisture.

It has been previously proposed to utilize nuclear magnetic resonance (NMR) for moisture determination. The NMR method is essentially a spectroscopic method whereby electromagnetic effects accompany the reorientation of nuclear moment under a specified set of conditions. In the determination of moisture only one absorption band, that of the hydrogen nuclei, is utilized. These hydrogen nuclei can be described as behaving like small precessing magnets. When they are placed in a steady magnetic field these nuclear magnets take one of two allowed orientations relative to the steady magnetic field direction. Since the magnetic moment of the nucleus is at an angle with the field in these two energy states, the nuclei are subjected to a torque; as a consequence they precess around the direction of the steady field with a frequency F. If the nuclei are exposed to an additional external radio-frequency (R-F) magnetic field oriented at right angles to the steady field, the protons will be made to reorient or "flip" when the R-F field has a frequency F. This forced reorientation absorbs energy from the R-F field. In general, NMR absorption occurs over a band of frequencies. This band is narrow for liquids and broad for solids. It is this fact which makes it possible to distinguish, in many cases, the protons of water from those of the solid constituents of agricultural materials. See for example: G. A. Persyn et al, "Transient NMR Quantitative Measurements" *Journal of the American Oil Chemists' Society, Volume 48,* p. 67–69, February, 1971; Miller et al, "Determination of Moisture by Nuclear Magnetic Resonance and Oven Methods in Wheat, Flour, Doughs, and Dried Fruits" *Food Technology,* p. 142–145, May, 1963; Rollwitz et al, "On-Stream NMR Measurements and Control" *Journal of the American Oil Chemists' Society, Volume* 48, p. 59–66, February, 1971.

U.S. Pat. No. 3,045,175 describes the use of NMR in the nondestructive analysis of the moisture of starch. U.S. Pat. No. 2,999,381 describes the measurement of moisture in tobacco by employing a NMR moisture gage, a weighing scale and read out device to measure directly the percentage by weight the moisture in tobacco. U.S. Pat. No. 2,948,845 describes an apparatus for determining the moisture content of a moving sheet of material by measuring NMR. These previous systems have certain shortcomings. The major problem with NMR results in the discrepancy caused by the presence of oil or other nonaqueous liquids which is detected and measured in the NMR system along with water. In many of the food systems listed above, nonaqueous liquids are present.

An important major objective of the invention is to eliminate this shortcoming of NMR measurements.

Another aspect of the invention is the proposal for using phase angle measurements exhibited by a test specimen subjected to variable e.m.f. stimulation for moisture measurements and to utilize such measurements in conjunction with NMR measurements.

THE OBJECTS

The primary objects are to provide (a) a process and apparatus for continuous accurate moisture control of food products especially those undergoing continuous or semi-continuous processing, (b) accurate measurement and control whether or not non-aqueous liquids are present, (c) rapid, substantially instantaneous control regardless of the presence of salts in an ionized condition, (d) satisfactory tolerance to non-uniform distribution of water in the product sample, (e) satisfactory for use in connection with products being pumped through pipes, and (f) suited for use with a variety of food products.

SUMMARY OF THE INVENTION

The moisture content of a food product is determined and preferably used to control its total moisture content by adding water or solids as needed. The moisture content is determined by continuously sensing the phase angle resulting from the application of an alternating current of a selected frequency to the product. In some food products the phase angle and impedance are used with an NMR liquid content signal. These measurements are fed to a computer or automatic data processing means which determines the moisture content. The moisture content thus computed is a function of the applied frequency in Hertz, the phase angle in degrees expressed from −90° through 0° to +90° and optionally the impedance in Ohms and the NMR liquid content. The resulting output from the computer which varies as the true moisture content is usually used to control the addition of water or solids from the food material to thereby regulate the moisture present.

The apparatus comprises electrodes connected to the product, a source of alternating current connected thereto, phase angle and impedance measuring means, data processing means and optionally an NMR liquid content meter. Interfaces are provided as required.

THE FIGURES

FIG. 1 is a schematic electrical diagram of the invention.

FIG. 2 is a schematic electrical diagram of another form of the invention, and

FIG. 3 is a schematic view of the vector impedance meter used for determining phase angle and impedance.

DESCRIPTION OF THE PREFERRED EMBODIMENTS

As seen in the Figures, numeral 10 designates diagramatically a NMR sensor pick-up which consists in this instance of an enclosure 12 for the product being measured 14. The enclosure is a pipe through which the product 14 is pumped during processing. The following products are typical of those with which the invention can be used: biscuit and bread dough, batters including cake, pancake, biscuit batter, non-flour containing foods including applesauce, peanutbutter, applebutter, jam, jelly, cooked mashed potato, pudding, frosting, mayonnaise, etc.

The pipe 12 is positioned between the pole pieces 15a and 15b of magnet 16. The product in the pipe 12 is located within a radio frequency sampling coil 28 which is connected by conductors 30 and 32 to an NMR instrument 34. The product is in this way subjected to an intense radio frequency field which is perpendicular to the magnetic field developed in the gap of pole pieces 15a and 15b of magnet 16. Modulation coils 18 and 20 envelope pole pieces 15a and 15b respectively so that the otherwise steady magnetic field is amplitude modulated by the audiofrequency energy supplied for modulation source 22 which is connected thereto by conductors 24 and 26. The NMR instrument 34 can be any pulsed or continuous NMR devices commercially available. Pulsed NMR is however, greatly preferred because with pulsed NMR all of the nuclei are activated whereas with continuous NMR measurement a smaller number of nuclei are activated. Thus, pulsed NMR provides much greater sensitivity. The pipe 12 is made of a poorly conductive material with no hydrogen nuclei present such as beryllium or of a nonconductor e.g. teflon or glass.

Any of several commercially available NMR analyzers can be employed such as the NMR Process Analyzer designated Praxis-PR-102 manufactured by the Praxis Corporation of San Antonio, Texas and described more fully in the *Praxis Operating and Service Manual* printed by the Praxis Corporation, 1971, which is incorporated herein by reference. Essentially the NMR analyzer uses the transient nuclear magnetic resonance technique to obtain hydrogen signals from both the liquids and solids in the sample. Operating the Praxis instrument at 30 MHZ provides excellent sensitivity. The Praxis instrument which was used in conducting tests carried out in the development of the present invention has five different pulse functions at 90°, 90° to −90°, 90° to −180°, 180° to −90°, and 180°. Other NMR units are commercially available. One such unit is the NMR instrument manufactured by Bruker Magnetic Incorporated, Burlington, Mass.

The pulsed NMR unit such as the one described herein requires a transmitter for generating the $H_1RF$ field, a preamplifier-receiver-detector unit for processing the nuclear signal and sample circuitry to contain the sample and to couple the sample to both the transmitter and the receiver. The requirements for these various units are different. The pulsed NMR transmitter must generate kilowatts of power during a pulse in order to give an $H_1$ in the range of 10–400G at the sample. On the other hand, a continuous wave transmitter usually generates much less than 1 watt since $H_1$ of $10^{-4}G$ is all that is required in the typical continuous wave unit. Further details of pulsed NMR spectrometers are given, for example, in *Pulse and Fourier Transform NMR* by Farrar et al Academic Press, 1971, which is incorporated herein by reference.

The NMR unit 34 is connected by conductor 36 to an analog-digital interface 38 (also known as a transient recorder) for making a permanent or semi-permanent record of a transient electronic signal. One example of a suitable instrument of this type is the transient recorder Model 802 manufactured by Biomation Incorporated, Palo Alto, California and described in U.S. Pat. No. 3,662,380 which is incorporated herein by reference. The transient recorder belongs to a class of electronic instruments using digital techniques to record a pre-selected section of an analog signal as it varies in time. Thus, the wave shape during the selected period of time is recorded and held in the instrument's memory until a new recording is made or power is removed. While the information is stored in the instrument's memory it can be viewed as a reconstructed analog signal or as an oscilloscope or X-Y display. It can also be the output as a reconstructed analog signal to a strip chart or YT record for making a permanent paper record or as an alternative, the output can be in digital form and can be hand fed to a digital recorder or directly to a computer for signal analysis or processing.

Briefly, the transient recorder 38 received the input signal through conductor 36 and feeds the input signal through an input amplifier. A trigger to initiate the sweep can be provided externally or can be derived from the input signal itself using a trigger level and slope control similar to those on most oscilloscopes. From the input amplifier the signal is fed to an analog-to-digital converter unit and then to a digital memory both of which receive signals from the timing and control circuit operated by the input from the signal itself using the trigger level and slope control. The output of the digital memory is fed through conductor 40 when switch 41 is closed to a digital computer 42. Further details of construction of the transient recorder i.e. the A/D interface 38, are fully presented in the *Operating and Service Manual for the model 802 transient recorder* printed by the Biomation Corporation, Palo Alto, Calif. which is incorporated herein by reference. Other transient recorders can be used if desired, for example those manufactured by Tecktronix Incorporated, Beaverton, Ore.; Gould Incorporated, Cleveland, Ohio; or Aminco, Silver Springs, Md. Since the transient recorder per se performs no part of the present invention, the details of construction will not be presented herein.

The numeral 48 indicates generally a vector impedance sensory unit which consists of a container in this instance a pipe or tube seen in cross section containing the product 14 that is being evaluated. Ordinarily the product 14 passes continuously through the pipe 50 in a direction normal to the plane of the drawing. The pipe 50 is provided with an opening 52 at the top which is sealed by means of a cover formed from plexiglass or other nonconductor 56 to which are secured electrodes 58 and 60 having binding posts 62 and 64 coupled respectively by conductors 67 and 68 to a vector impedance meter 70. The electrodes 58 and 60 are preferably formed from a conductor such as aluminum or other metal which will not be active chemically under the conditions of use. If aluminum is used the conductors can be about 0.40 inches thick. With a plexiglass cover 56 measuring 3 inches by ½ inch, the aluminum electrodes can be 1½ inches long times ⅜ inches wide spaced 13/16 inches apart. In a typical application, the distance from the bottom of the plexiglass to the lower tip of each electrode is 1 3/16 inches.

It was surprising to discover that when an alternating current is applied to the fluid food systems such as dough or mashed potatoes, in general any conductive fluid or semi-fluid organic material, there exists a lag in phase between the capactive and the resistive components that exist in response to the applied EMF. It was discovered that the phase angle is for the most part negative. However, on occasion, particularly at the higher frequencies, it is positive in sign. Thus, these fluid or semii-fluid conductive organic materials behave at lower frequencies somewhat as a combined resistance and capacatance while at the higher frequencies they behave somewhat as an R.C.L. circuit (resistance, capacitance, and inductance).

A typical vector impedance meter is shown in simplified block diagram in FIG. 3 which illustrates the operation in the first of three decade ranges of the Z range switch 200. As seen in the figure, an oscillator 202 connected by conductor 203 to AGC amplifier 204 provides a test signal within the frequency range of 5HC to 500 kHC as determined by a frequency range switch 206. The AGC amplifier 204 holds the signal current through the Z range switch 200 through conductor 208 and the tests are made at a constant level by means of an ALC feedback loop 210. This current is applied to a transresistance amplifier 212 through conductor 214 which provides an output voltage proportional to the current flowing in the test sample 14. The voltage is amplified, filtered and forwarded through relay contacts 216 to the ALC amplifier detector 218.

In the first three impedance ranges, the voltage across the sample 14 is applied to a differential amplifier 220 through two sets of relay contact 222 and 224 via conductors 226 and 228. The output of the differential amplifier 220 is amplified, filtered and forwarded through relay contacts 230 to a Z magnitude detector 232.

When the impedance meter is operated in the upper four ranges of the Z range switch 200, the relay contacts switch to their alternate positions and the voltage is held constant while the current through the sample 14 is measured. This current is applied to the Z magnitude detector through relay contacts 230. The output from the detector 230 and 232 is inversely proportional to the impedance of the sample which is indicated on the Z magnitude meter 234. The phase angle is measured in the same way in both the constant current and constant voltage modes of operation. Signals from the current and voltage channels are filtered to improve signal-to-noise ratio and then converted to pulses in Schmitt trigger circuits 236. The output pulses from the Schmitt triggers 236 drive through conductors 238 and 239 to binary phase detector 240 which provides an output voltage proportional to the phase difference between the two channels. A 0-center phasing angle meter 242 reads this voltage as phase angle in degrees. The output of the phase detector 240 is also fed through conductor 72 to an interface 76 and the Z magnitude or impedance is fed through a conductor 74 to the A/D interface 76. Further details of construction in operation of a typical vector impedance meter are set forth in *Operating and Service Manual Vector Impedance Meter 4800A*, Hewlett Packard Company, 1968, Rockaway, N.J. which is incorporated herein by reference. Other suitable vector impedance meters are described for example *Electronic Measurements and Laboratory Practice*, Prentice-Hall, 1973, see for example pages 185 and 369. A part of the vector meter function can be performed by capacitance bridges such as those manuactured by General Radio Company and Boonton Electronics Incorporated.

The vector impedance meter 70 measures the magnitude and phase angle of the impedance at the frequency applied to a sample connected to the inputs of the meter. The desired frequency of excitation is dialed in and the magnitude of the phase angle and impedance are displayed by the panel meters 234 and 242 while at the same time being fed to the interface 76. In the development of the present invention the following stimulation frequencies were used: 15.92Hz, 159.2Hz, 1592Hz, 15920Hz, and 159200Hz.

It has been breifly mentioned above that the capacitance bridges can be substituted for the vector impedance meter described above although the latter is preferred. The vector impedance meter is preferred primarily because a capacitance bridge measures only C. A and L would have to be found with additional equipment. There are two general forms in which capacitance bridges are manufactured commercially at present. The first type is an instrument containing two capacitance comparison bridges; a series-comparison type and a parallel capacitance type. Most such bridges contain an internal AC source at a single fixed frequency. A few others provide multiple internal frequencies. However, almost all contain provisions for connecting additional external AC sources so that the instrument can be used at other frequencies as well. Typical capacitance values which can be measured using capacitance bridges range from 1pF to 1000$\mu$F to accuracies of 1%. Another type of bridge which can be used is called the universal bridge and is capable of measuring R, L, as well as C they usually have five or six built in bridge circuits with appropriate switching to connect them. For measuring capacitance two of these bridges are the series-comparison and parallel-comparison bridges. They also usually contain a fixed internal AC source as well as having the option of connecting additional external AC signals.

The analog-digital interface 76 can be similar to or identical to the interface 38. The phase angle and impedance signals are fed to the automatic digital computer 42 through conductors 78 and 80 respectively from interface 76.

The digital computer 42 can comprise any suitable or scientific or process control computer for example models manufactured by Digital Equipment Company of Maynard, Mass. of the PDP8 series or the PDP11 series. Other suitable computers will be apparent to those skilled in the art. The computer 42 performs the calculations described below and set forth in the polynomial equations for the purpose of computing moisture content from the NMR and vector impedance meter readings or from the vector impedance meter alone in the case of certain samples in which case the switch 41 is opened. The output of the digital computer 42 varies as the true moisture content of the specimen 14 and is connected by a conductor 43 to a valve controller 45 that is coupled to valve 47 for regulating the flow of water through a pipe 49 to be mixed with the product 14. This corrects the moisture content of the product by bringing it to the desired level.

The operation of the apparatus will be described in detail below after a brief reference to an alternate form of the apparatus shown in FIG. 2. As seen in FIG. 2, the pulsed NMR unit 34 is connected by conductor 102 to the analog-to-digital converter 38 which is in turn connected by conductor 104 to a digital storage unit 106. The output of 106 is connected by conductor 108 to a digital-to-analog storage 110 and the NMR signal is fed through conductor 112 to an analog computer 100. The analog computer 100 is connected by conductor 103 to the controller 45 to regulate the addition of water as described above. The vector impedance meter 70 is connected directly to computer 100 by conductors 114 and 116. The operation of the apparatus in FIG. 2 is the same essentially as that is FIG. 1 except the data is maintained in analog form. All runs should all be made with the product sample at a constant temperature e.g. 70°F.

The moisture is calculated as a function of the applied frequency in Hertz, the phase angle in degrees from −90° to +90°, the impedance in Ohms, and optionally NMR liquid content in % liquid. The computer 42 is programmed conventionally to compute the unknown moisture content Y. Each term of the polynomial equation for moisture is multiplied by a particular constant that is unique for each type of food. The important point is that moisture is expresssed as the function of the frequency, (optionally impedance) phase angle either with or without NMR liquid content. The NMR liquid content term as mentioned above is used for products which contain significant amounts of nonaqueous liquid. The equation can be determined by what is commonly known as the least squares method to obtain the best fit. A typical general equation for moisture is as follows:

$$Y = KX_1X_3 + K_1(X_1)^2 + K_2X_2X_3 + K_3X_1 + K_4X_1 + K_5X_3(X_4)^2 + K_6X_1X_2$$

wherein
 $Y$ = computed moisture
 $K$ to $K_6$ = constants
 $X_1$ = log frequency in Hertz
 $X_2$ = phase angle in degrees
 $X_3$ = impedance
 $X_4$ = % liquid measured by NMR The order of importance of the terms in the equation is as follows in descending order: $X_1X_3$, $(X_1)^2$, $X_2X_3$, $X_1$, $X_3$, $(X_4)^2$ and $X_1X_2$ which contributed the following percentages of accuracy respectively: 20%, 16%, 16%, 14%, 11%, 2%, and 2%.

The invention will be better understood by reference to the following examples.

EXAMPLE I

Utilizing the apparatus shown and described in FIG. 1 and making use of NMR data as well as phase angle and impedance data, tests were run on the dough composition of Table I and having a moisture content of about 38% to 43%. Twenty-five samples of the dough were evaluated and a comparison was made between moisture content as determined by a standard vacuum oven moisture test in Tables II and III. In the third to the last column of TAble III below the moisture content determined by the invention is given.

TABLE I

| Dough * | % Flour[1] | % Water | % Starch[2] | % Shortening[3] |
|---|---|---|---|---|
| 1 | 58.97 | 38.61 | 1.04 | 1.38 |
| 2 | 56.61 | 41.06 | 1.00 | 1.33 |
| 3 | 56.16 | 36.77 | 5.75 | 1.32 |
| 4 | 54.02 | 39.18 | 5.53 | 1.27 |
| 5 | 55.29 | 36.20 | 0.97 | 7.54 |
| 6 | 53.21 | 38.59 | 0.94 | 7.26 |
| 7 | 52.81 | 34.57 | 5.41 | 7.21 |
| 8 | 50.91 | 36.93 | 5.21 | 6.95 |
| 9 | 58.97 | 38.61 | 1.04 | 1.38 |
| 10 | 56.61 | 41.06 | 1.00 | 1.33 |
| 11 | 56.16 | 36.77 | 5.75 | 1.32 |
| 12 | 54.02 | 39.18 | 5.53 | 1.27 |
| 13 | 55.29 | 36.20 | 0.97 | 7.54 |
| 14 | 53.21 | 38.59 | 0.94 | 7.26 |
| 15 | 52.81 | 34.57 | 5.41 | 7.21 |
| 16 | 50.91 | 36.93 | 5.21 | 6.95 |
| 17 | 54.64 | 37.71 | 3.28 | 4.37 |
| 18 | 56.18 | 35.96 | 3.37 | 4.49 |
| 19 | 53.19 | 39.36 | 3.19 | 4.26 |
| 20 | 56.50 | 38.98 | none | 4.52 |
| 21 | 52.91 | 36.51 | 6.35 | 4.23 |
| 22 | 57.14 | 39.43 | 3.43 | none |
| 23 | 54.64 | 37.71 | 3.28 | 4.37 |
| 24 | 54.64 | 37.71 | 3.28 | 4.37 |
| 25 | 54.64 | 37.71 | 3.28 | 4.37 |

[1] bleached hard wheat flour
[2] wheat starch, ungelatinized
[3] beef tallow containing BHA and citric acid as freshness preservers Tables II and III contain the data obtained in the test series on samples 1 to 25 of Table I. The impedance and phase angle data were run at five frequencies indicated from 15.9Hz to 159,200Hz.

TABLE II

EXPERIMENTAL DATA

| Frequency Sample | 159200Hz Phase Angle-Impedance | | 15920Hz Phase Angle-Impedance | | 1592Hz Phase Angle-Impedance | |
|---|---|---|---|---|---|---|
| 1 | −1.53 | 460 | −2.47 | 490 | −7.40 | 590 |
| 2 | +0.67 | 450 | −0.27 | 477 | −5.67 | 543 |
| 3 | −2.00 | 560 | −1.13 | 583 | −4.50 | 627 |
| 4 | +0.43 | 457 | −0.07 | 480 | −5.07 | 537 |
| 5 | −2.53 | 580 | −1.23 | 600 | −4.10 | 650 |
| 6 | +0.90 | 467 | +1.27 | 483 | −2.47 | 513 |
| 7 | −3.17 | 617 | −2.10 | 647 | −4.83 | 707 |
| 8 | +0.17 | 487 | +0.70 | 507 | −2.63 | 543 |
| 9 | −2.13 | 527 | −2.33 | 557 | −6.53 | 627 |
| 10 | +1.87 | 417 | +1.07 | 443 | −4.13 | 493 |
| 11 | −3.50 | 613 | −3.07 | 650 | −5.87 | 733 |
| 12 | −0.03 | 463 | −0.93 | 500 | −5.80 | 570 |
| 13 | −4.27 | 643 | −3.30 | 677 | −5.90 | 740 |
| 14 | 0.00 | 490 | +0.13 | 510 | −3.93 | 557 |
| 15 | −4.47 | 707 | −2.70 | 750 | −4.90 | 810 |
| 16 | −1.27 | 537 | −0.40 | 553 | −3.67 | 590 |
| 17 | +0.93 | 463 | +1.57 | 477 | −1.73 | 510 |
| 18 | −1.97 | 574 | −0.57 | 583 | −3.10 | 617 |
| 19 | +2.63 | 430 | +3.03 | 440 | −0.33 | 473 |
| 20 | +1.10 | 467 | +1.97 | 477 | −0.83 | 503 |
| 21 | −0.80 | 527 | +0.13 | 537 | −3.03 | 570 |

TABLE II-continued

| | | | | | | |
|---|---|---|---|---|---|---|
| 22 | +2.20 | 450 | +2.73 | 450 | −0.63 | 473 |
| 23 | +0.60 | 480 | +1.30 | 490 | −1.70 | 520 |
| 24 | +0.27 | 493 | +1.43 | 503 | −0.90 | 527 |
| 25 | +0.30 | 483 | +1.07 | 497 | −2.10 | 530 |

| Frequency | 159.2Hz | | 15.92Hz | | | |
|---|---|---|---|---|---|---|
| Sample | Phase Angle-Impedance | | Phase Angle-Impedance | | NMR | |
| 1 | −20.80 | 920 | −33.90 | 2150 | 47.43 | |
| 2 | −21.17 | 780 | −35.40 | 1833 | 46.43 | |
| 3 | −17.20 | 810 | −32.77 | 1750 | 39.52 | |
| 4 | −21.70 | 750 | −36.10 | 1825 | 47.38 | |
| 5 | −15.13 | 810 | −31.17 | 1600 | 53.96 | |
| 6 | −18.27 | 853 | −34.77 | 1517 | 40.97 | |
| 7 | −15.33 | 907 | −30.70 | 1783 | 44.71 | |
| 8 | −16.73 | 683 | −33.00 | 1467 | 52.74 | |
| 9 | −20.37 | 867 | −35.00 | 2000 | 46.73 | |
| 10 | −22.53 | 693 | −36.87 | 1733 | 41.73 | |
| 11 | −17.60 | 973 | −32.07 | 2100 | 42.56 | |
| 12 | −19.40 | 800 | −33.43 | 1757 | 40.22 | |
| 13 | −18.27 | 980 | −33.90 | 2150 | 43.71 | |
| 14 | −18.77 | 747 | −34.27 | 1683 | 46.88 | |
| 15 | −15.83 | 1000 | −30.97 | 1983 | 45.89 | |
| 16 | −16.43 | 757 | −32.37 | 1568 | 43.73 | |
| 17 | −16.37 | 640 | −33.17 | 1357 | 43.73 | |
| 18 | −14.43 | 750 | −30.70 | 1483 | 43.72 | |
| 19 | −16.50 | 587 | −34.17 | 1317 | 47.16 | |
| 20 | −14.57 | 610 | −31.97 | 1217 | 42.62 | |
| 21 | −15.27 | 717 | −30.47 | 1423 | 47.16 | |
| 22 | −16.77 | 600 | −34.47 | 1333 | 37.73 | |
| 23 | −15.40 | 645 | −31.70 | 1305 | 44.81 | |
| 24 | −13.40 | 627 | −30.60 | 1200 | 47.16 | |
| 25 | −16.43 | 663 | −32.73 | 1383 | 44.88 | |

TABLE III

COMPARISON OF ESTIMATED AND OVEN MOISTURE VALUES

| Sample | % Moisture 159200Hz | Deviation | % Moisture 15920Hz | Deviation | % Moisture 1592Hz | Deviation |
|---|---|---|---|---|---|---|
| 1 | 44.38 | +1.64 | 44.80 | +2.06 | 43.70 | +0.96 |
| 2 | 43.86 | −2.22 | 44.38 | −1.70 | 44.07 | −2.01 |
| 3 | 42.32 | +0.68 | 42.47 | +0.83 | 42.35 | +0.71 |
| 4 | 43.68 | −0.73 | 44.16 | −0.25 | 43.91 | −0.50 |
| 5 | 40.91 | +0.37 | 40.99 | +0.45 | 40.60 | +0.06 |
| 6 | 43.86 | +0.52 | 44.03 | +0.69 | 43.95 | +0.61 |
| 7 | 40.92 | +1.13 | 40.92 | +1.13 | 40.45 | +0.66 |
| 8 | 42.48 | +0.07 | 42.72 | +0.31 | 42.45 | +0.04 |
| 9 | 42.80 | −0.79 | 43.13 | −0.46 | 42.67 | −0.92 |
| 10 | 44.70 | −1.33 | 45.12 | −0.91 | 44.91 | −1.12 |
| 11 | 41.34 | −0.32 | 41.43 | −0.23 | 40.52 | −1.14 |
| 12 | 44.20 | +0.34 | 44.47 | +0.61 | 44.00 | +0.14 |
| 13 | 40.81 | −0.25 | 40.79 | −0.27 | 40.31 | −0.75 |
| 14 | 42.93 | −0.23 | 43.33 | +0.17 | 43.10 | −0.06 |
| 15 | 39.03 | −0.20 | 38.54 | −0.69 | 38.23 | −1.00 |
| 16 | 42.36 | +0.67 | 42.51 | +0.82 | 42.53 | +0.84 |
| 17 | 43.57 | +0.65 | 43.89 | +0.97 | 43.57 | +0.65 |
| 18 | 41.66 | +0.05 | 41.95 | +0.34 | 41.72 | +0.11 |
| 19 | 43.62 | −0.74 | 44.11 | −0.25 | 43.68 | −0.68 |
| 20 | 43.58 | −0.44 | 43.82 | −0.20 | 43.49 | −0.53 |
| 21 | 42.19 | +0.16 | 42.60 | +0.57 | 42.46 | +0.43 |
| 22 | 43.84 | −1.02 | 44.59 | −0.27 | 44.43 | −0.43 |
| 23 | 43.13 | −0.13 | 43.56 | +0.30 | 43.26 | 0.00 |
| 24 | 42.71 | +0.33 | 42.99 | +0.61 | 42.64 | +0.26 |
| 25 | 43.16 | −0.04 | 43.46 | +0.26 | 43.17 | −0.03 |

| Sample | % Moisture 159.2Hz | Deviation | % Moisture 15.92Hz | Deviation | Moisture % Mean | Oven % Moisture | Deviation |
|---|---|---|---|---|---|---|---|
| 1 | 42.38 | −0.36 | 42.13 | −0.61 | 43.48 | 42.74 | +0.74 |
| 2 | 44.15 | −1.93 | 44.19 | −1.89 | 44.13 | 46.08 | −1.95 |
| 3 | 42.51 | +0.87 | 42.60 | +0.96 | 42.45 | 41.64 | +0.81 |
| 4 | 44.62 | +0.21 | 44.73 | +0.32 | 44.22 | 44.41 | −0.19 |
| 5 | 40.51 | −0.03 | 40.68 | +0.14 | 40.74 | 40.54 | +0.20 |
| 6 | 42.39 | −0.95 | 44.58 | +1.24 | 43.76 | 43.34 | +0.42 |
| 7 | 40.03 | +0.24 | 40.40 | +0.61 | 40.54 | 39.79 | +0.75 |
| 8 | 42.95 | +0.54 | 42.53 | +0.12 | 42.63 | 42.41 | +0.22 |
| 9 | 42.81 | −0.78 | 43.54 | −0.05 | 42.99 | 43.59 | −0.60 |
| 10 | 45.95 | −0.08 | 45.88 | −0.15 | 45.31 | 46.03 | −0.72 |
| 11 | 40.49 | −1.17 | 40.78 | −0.88 | 40.91 | 41.66 | −0.75 |
| 12 | 43.58 | −0.28 | 43.09 | −0.77 | 43.87 | 43.86 | +0.01 |
| 13 | 40.67 | −0.39 | 42.40 | +1.34 | 41.00 | 41.06 | −0.06 |
| 14 | 43.46 | +0.30 | 43.47 | +0.31 | 43.26 | 43.16 | +0.10 |
| 15 | 38.97 | −0.26 | 39.85 | +0.62 | 38.92 | 39.23 | −0.31 |
| 16 | 42.58 | +0.89 | 42.50 | +0.81 | 42.50 | 41.69 | +0.81 |
| 17 | 44.07 | +1.15 | 43.62 | +0.70 | 43.74 | 42.92 | +0.82 |
| 18 | 41.83 | +0.22 | 41.56 | −0.05 | 41.74 | 41.61 | +0.13 |
| 19 | 44.43 | +0.07 | 44.11 | −0.25 | 43.99 | 44.36 | −0.37 |
| 20 | 43.89 | −0.13 | 43.34 | −0.68 | 43.62 | 44.02 | −0.40 |
| 21 | 42.37 | +0.34 | 41.36 | −0.67 | 42.20 | 42.03 | +0.17 |
| 22 | 45.12 | +0.26 | 44.92 | +0.06 | 44.58 | 44.86 | −0.28 |

TABLE III-continued

| 23 | 43.56 | +0.30 | 42.75 | −0.51 | 43.25 | 43.26 | −0.01 |
| 24 | 42.90 | +0.52 | 42.26 | −0.12 | 42.70 | 42.38 | +0.32 |
| 25 | 43.71 | +0.51 | 43.19 | −0.01 | 43.34 | 43.20 | +0.14 |

On the basis of the experimental data shown in Table II, an empirical equation was derived by the least squares method for estimating the moisture, Y, of doughs from vector impedance measurements and NMR liquid content. The equation generated for the dough system of samples 1 through 25 is as follows:

$$Y = 38.19202 + 8.36100 (X_1) - 0.01391 (X_3) - 0.84146 (X_1)^2 - 0.00081 (X_1)^2 - 0.03804 (X_1)(X_2) - 0.00290 (X_1)(X_3) - 0.00045 (X_2)(X_3)$$

wherein
$Y$ = estimated % moisture
$X_1$ = log frequency in Hertz
$X_2$ = phase angle in degrees
$X_3$ = impedance
$X_4$ = % liquid as measured on the NMR The "oven" moisture which is regarded as the true moisture content was determined by placing an accurately weighed 2 gram sample of the material into a previously dried and tared moisture dish. The dish was placed in a vacuum oven at 67.5° Centigrade for 16 hours. The pressure was not greater than 25MM of mercury. At the end of the 16 hours the dish was covered and removed to a desiccator to cool and weighed to determine the loss of moisture. The use of multiple frequencies was tried to determine at which frequency the greatest accuracy could be obtained. It appears that the frequencies of 159.2Hz or 159,200Hz provide the greatest accuracy.

It can be seen that 95% of the estimated values were within plus or minus 1.54% of the oven moisture values. The NMR value in addition to the phase angle and impedance values makes possible greatly improved accuracy in the case of doughs containing fat.

The output of the computer 42 is fed to a meter to indicate moisture directly and is also sent to the controller 45 to control water addition continuously to bring the moisture level to the selected value.

EXAMPLE II

The apparatus of FIG. 1 is used with the switch 41 open, in other words with only the phase angle and frequency information on the following dough formulas.

TABLE IV

PHASE ANGLE AND FARINOGRAPH PEAKS FROM FLOUR — WATER DOUGHS
(NO STARCH OR SHORTENING USED)

| Dough Number | % Flour₁ | % Water Added | Phase Angle at 15,920 Hz |
|---|---|---|---|
| 1 | 70 | 30 | −5.1 |
| 2 | 65 | 35 | −4.0 |
| 3 | 69 | 31 | −5.5 |
| 4 | 68 | 32 | −5.6 |
| 5 | 67 | 33 | −5.7 |
| 6 | 66 | 34 | −4.9 |
| 7 | 60 | 40 | −0.1 |
| 8 | 64 | 36 | −2.6 |
| 9 | 63 | 37 | −2.0 |
| 10 | 62 | 38 | −1.1 |
| 11 | 61 | 39 | 0.0 |
| 12 | 55 | 45 | +2.1 |
| 13 | 59 | 41 | +1.5 |

₁bleached hard wheat flour

A total of 13 runs were made generally as described in Example 1 except that no NMR data was used with the doughs at 70° Fahrenheit using the following polynomial equation which was determined by the least squares method.

$$Y = 53.62736 + 2.06298 (X_2) - 0.41668 (X_1)^2 + 0.04193 (X_2)^2 - 0.27447 (X_1 X_2)$$

Wherein
$Y$ = estimated % moisture
$X_1$ = log frequency
$X_2$ = phase angle

The values determined by the computer 42 in each of five frequencies is given in Table V below together with the deviations from the vacuum oven obtained moisture values.

TABLE V

COMPARISON OF ESTIMATED AND VACUUM - OVEN MOISTURES

| Sample | %Moisture 159200Hz | Deviation | %Moisture 15920Hz | Deviation | %Moisture 1592Hz | Deviation |
|---|---|---|---|---|---|---|
| 1 | 39.97 | +2.35 | 42.72 | +5.10 | 43.43 | +5.81 |
| 2 | 40.75 | −0.89 | 43.30 | +1.66 | 42.34 | +0.70 |
| 3 | 40.06 | +1.91 | 42.53 | +4.38 | 43.06 | +4.91 |
| 4 | 40.04 | +0.42 | 42.72 | +3.10 | 42.94 | +3.32 |
| 5 | 40.13 | +0.10 | 42.45 | +2.42 | 42.72 | +2.69 |
| 6 | 42.56 | −1.07 | 42.82 | +1.33 | 42.52 | +1.03 |
| 7 | 44.20 | −1.73 | 46.18 | +0.25 | 43.97 | −1.96 |
| 8 | 41.76 | −0.97 | 44.14 | +1.41 | 42.84 | +0.11 |
| 9 | 42.29 | −1.49 | 44.62 | +0.84 | 43.18 | −0.60 |
| 10 | 42.89 | −1.78 | 45.32 | +0.65 | 43.56 | −1.11 |
| 11 | 44.04 | −1.83 | 46.27 | +0.40 | 43.76 | −2.11 |
| 12 | 46.26 | −4.66 | 48.37 | −2.55 | 44.88 | −6.04 |
| 13 | 46.26 | −1.07 | 48.37 | +1.04 | 44.88 | −2.45 |

| Sample | %Moisture 159.2Hz | Deviation | %Moisture 15.92Hz | Deviation | Moisture % Mean | Oven % Moisture | Deviation |
|---|---|---|---|---|---|---|---|
| 1 | 38.93 | +1.31 | 38.61 | +0.99 | 40.73 | 37.62 | +3.11 |
| 2 | 40.65 | −0.99 | 45.24 | +3.60 | 42.46 | 41.64 | +0.82 |
| 3 | 38.93 | +0.78 | 38.69 | +0.54 | 40.65 | 38.15 | +2.50 |
| 4 | 38.96 | −0.66 | 39.86 | +0.24 | 40.90 | 39.62 | +1.28 |
| 5 | 39.11 | −0.92 | 40.70 | +0.67 | 41.02 | 40.03 | +0.99 |
| 6 | 39.57 | −1.92 | 42.58 | +1.09 | 42.01 | 41.49 | +0.52 |

TABLE V-continued

| | | | | | | | |
|---|---|---|---|---|---|---|---|
| 7 | 40.76 | −5.17 | 44.60 | −1.33 | 43.94 | 45.93 | −1.99 |
| 8 | 40.65 | −2.08 | 44.80 | +2.07 | 42.84 | 42.73 | +0.11 |
| 9 | 40.44 | −3.34 | 44.35 | +0.57 | 42.98 | 43.78 | −0.80 |
| 10 | 41.35 | −3.32 | 45.63 | +0.96 | 43.75 | 44.67 | −0.92 |
| 11 | 41.23 | −4.64 | 45.37 | −0.50 | 44.13 | 45.87 | −1.74 |
| 12 | 46.69 | −4.23 | 50.80 | −0.12 | 47.40 | 50.92 | −3.52 |
| 13 | 46.69 | −0.64 | 50.80 | +3.47 | 47.40 | 47.33 | +0.07 |

Of the five frequencies studied, the computed moistures were closest to the values obtained by the oven method at 15.92Hz and 159,200Hz. At 15.92Hz the largest deviation was +3.60, while for 159,200Hz the largest deviation was −4.66. An average of the estimates made at the five frequencies was also computed. The largest deviation of the mean values was −3.52. Using the mean estimate obtained at the five frequencies one can compute the moisture content of the doughs to within plus or minus 3.7% of the vacuum oven value.

EXAMPLE III

The moisture content of peanut butter, mayonnaise, cake batter, and frosting are computed as described above in connection with Example I.

EXAMPLE IV

A run is made as in Example II except that the impedance is also measured as in Example I and used as an additional variable to compute moisture content.

EXAMPLE V

The moisture content of strawberry jam and cooked mashed potato is computed as described above in conection with Example IV.

What is claimed is:

1. A process for determining the moisture content of a food comprising applying an alternating current to the food product, measuring the impedance in Ohms and the phase angle in degrees expressed from minus 90° to plus 90°, measuring the NMR liquid content and expressing the moisture content as a function of the applied frequency in Hertz, the phase angle in degrees, the impedance in Ohms, and the NMR liquid content.

2. A process for determining the moisture content of a food which contains moisture with automatic data processing means comprising applying an alternating current to the food product, measuring the impedance in Ohms and the phase angle in degrees expressed from minus 90° to plus 90°, measuring the NMR liquid content, feeding the values thus measured to said automatic data processing means and computing the moisture content as a function of the applied frequency in Hertz, the phase angle in degrees, the impedance and the NMR percent liquid content.

3. A method of measuring the moisture content of dough products containing a quantity of cereal flour, fat and moisture said process comprising applying an alternating current of a selected frequency to the dough product, sensing the impedance and phase angle resulting therefrom, measuring the NMR liquid content of the dough, and using the impedance, phase angle and NMR liquid content thus sensed to compute the moisture content, the moisture content being thereby computed as a function of the applied frequency in Hertz, the phase angle in degrees expressed from minus 90° through zero to plus 90°, the impedance and the NMR liquid content in accordance with the general formula $$Y = KX_1X_3 + K_1(X_1)^2 + K_2X_2X_3 + K_3X_1 + K_4X_1 + K_5X_3(X_4)^2 + K_6X_1X_2,$$

wherein
$Y$ = computed moisture
$K$ to $K_6$ = constants
$X_1$ = log frequency in Hertz
$X_2$ = phase angle in degrees
$X_3$ = impedance
$X_4$ = % liquid measured by NMR.

4. The process of claim 3 wherein the moisture content thus calculated is used to control the addition of moisture or solids to the dough to bring the moisture level thereof to a preestablished level.

5. The process of claim 1 wherein the moisture content thus calculated is used to control the addition of moisture or solids to the dough to bring the moisture level thereof to a preestablished level.

* * * * *